(12) United States Patent  
Staeuber et al.

(10) Patent No.: US 8,812,094 B2  
(45) Date of Patent: Aug. 19, 2014

(54) CARDIOVERTER/DEFIBRILLATOR AND SIGNAL PROCESSING DEVICE FOR CLASSIFYING INTRACARDIAC SIGNALS

(75) Inventors: Philipp Staeuber, Berlin (DE); Andreas Neumann, Berlin (DE); Ulrich Busch, Berlin (DE); Peter Wohlgemuth, Chemnitz (DE)

(73) Assignee: Biotronik SE & Co. KG (DE)

( * ) Notice: Subject to any disclaimer, the term of this patent is extended or adjusted under 35 U.S.C. 154(b) by 130 days.

(21) Appl. No.: 13/023,894

(22) Filed: Feb. 9, 2011

(65) Prior Publication Data

US 2011/0196249 A1   Aug. 11, 2011

Related U.S. Application Data

(60) Provisional application No. 61/302,569, filed on Feb. 9, 2010.

(51) Int. Cl.
*A61B 5/02* (2006.01)
*A61B 5/04* (2006.01)

(52) U.S. Cl.
USPC ............ 600/518; 600/508; 600/509; 600/512

(58) Field of Classification Search
USPC .................................. 600/508–509, 512, 518
See application file for complete search history.

(56) References Cited

U.S. PATENT DOCUMENTS

| | | |
|---|---|---|
| 5,779,645 A | 7/1998 | Olson et al. |
| 2003/0004547 A1 | 1/2003 | Owen et al. |
| 2003/0023277 A1 | 1/2003 | Owen et al. |
| 2003/0032988 A1 | 2/2003 | Fincke |
| 2003/0055460 A1 | 3/2003 | Owen et al. |
| 2005/0137485 A1 | 6/2005 | Cao et al. |
| 2007/0021679 A1* | 1/2007 | Narayan et al. ............... 600/518 |
| 2007/0276276 A1 | 11/2007 | Cao et al. |

FOREIGN PATENT DOCUMENTS

EP     0848965 A2     6/1998

* cited by examiner

*Primary Examiner* — Nicole F Lavert
(74) *Attorney, Agent, or Firm* — Craig A. Fieschko, Esq.; DeWitt Ross & Stevens S.C.

(57) ABSTRACT

The invention relates to methods of differentiating between ventricular tachycardias (VTs) and supraventricular tachycardias (SVT) with the assistance of morphology detection, and signal processing devices implementing such methods.

20 Claims, 7 Drawing Sheets

CARDIOVERTER/DEFIBRILLATOR AND SIGNAL PROCESSING DEVICE FOR CLASSIFYING INTRACARDIAC SIGNALS

CROSS-REFERENCE TO RELATED APPLICATIONS

This application claims priority under 35 USC §119(e) to U.S. Provisional Patent Application 61/302,569 filed Feb. 9, 2010, the entirety of which is incorporated by reference herein.

FIELD OF THE INVENTION

The invention relates to a signal processing device for classifying intracardiac signals, and to a cardiac stimulator, in particular a cardioverter/defibrillator, having such a signal processing device. The cardiac stimulator may be provided in the form of a single-chamber cardiac stimulator, a biventricular cardiac stimulator, or the like.

BACKGROUND OF THE INVENTION

Implantable cardiac stimulators are in common use in the form of cardiac pacemakers or cardioverters/defibrillators. Such cardiac stimulators are used in treating disorders in the natural contraction of the chambers of a heart with the assistance of stimulation pulses and/or defibrillation shocks. Thus, such cardiac stimulators are usually connected to electrode lines having stimulation or defibrillation electrodes in a chamber of a heart, or in the immediate vicinity thereof.

In the chamber of a heart, a localized excitation of the cardiac muscle tissue (myocardium) propagates from an excitation site into the myocardium via conduction, and results in depolarization of the muscle cells, and thus in a contraction of the myocardium. After a brief period of time repolarization of the muscle cells, and thus relaxation of the myocardium, occurs. During the depolarization phase the cardiac muscle cells are insensitive to excitation, i.e., are refractory. The electrical potentials accompanying the depolarization and repolarization may be detected, and their variation over time, referred to as an electrocardiogram, may be evaluated.

Such natural (intrinsic) cardiac behavior events are detected by measuring the electrical potentials of the myocardium in one or more cardiac chambers, using sensing electrodes provided on one or more corresponding electrode lines. The sensing electrodes may also serve as stimulation electrodes, and may switch between use as stimulation electrodes and sensing electrodes. Typically, for the sensing, i.e., detection, of intrinsic events, a sensing electrode pair is provided which is formed by two adjacent electrodes, usually a tip electrode and an annular electrode, wherein the tip electrode is also used as a stimulation electrode. In this manner a bipolar measurement of an intracardiac electrocardiogram (IEGM) is obtained.

The electrodes typically detect electrical signals in the cardiac chamber in which the electrodes are situated. Detection of so-called "far-field electrocardiograms" is also possible, i.e., detection of electrical potentials of the myocardium whose origin is remote from the position of the electrode. For example, an electrode placed in the ventricle may also be used to detect signals from an atrium. Far-field electrocardiograms may be recorded using not only the electrodes provided for stimulation, but also by use of the shock coils provided for the delivery of defibrillation shocks. The opposite pole for signal detection may be another electrode, another shock coil, and/or the electrically conductive housing of an implantable cardiac stimulator.

During operation of the cardiac stimulator, the sensing electrodes are connected to corresponding sensing units which are designed to evaluate an electrocardiogram recorded via the sensing electrode(s), and in particular to detect intrinsic atrial or ventricular events, i.e., natural atrial or ventricular contractions. This is carried out, for example, by threshold value comparison, wherein an intrinsic event is detected within an intracardiac electrocardiogram when the voltage therein exceeds a suitably specified threshold value. The intrinsic atrial heart rate (atrial frequency) or ventricular heart rate (ventricular frequency) may be determined from the time sequence of atrial or ventricular events within the electrocardiogram.

Apart from the previously described characteristics of a cardiac pacemaker, an implantable cardioverter/defibrillator can also deliver a stronger current pulse to the heart, one which doesn't merely stimulate (depolarize) a small portion of the myocardium, and which instead depolarizes the greatest possible portion of the myocardium (and thus makes it refractory) in order to interrupt circulating excitation of the myocardium that is typical of fibrillation. Such a pulse is referred to as "defibrillation shock." This type of pulse is typically delivered via a defibrillation electrode having a large surface area compared to the stimulation or sensing electrode.

Such a defibrillation electrode is frequently implemented in the form of a shock coil on the exterior of the electrode line in the particular cardiac chamber. For example, besides a tip electrode or annular electrode for the stimulation and sensing, a ventricular electrode line may also have a ventricular shock coil, as well as a proximal shock coil located in the superior vena cava after implantation.

A defibrillation shock is generally delivered when the cardiac stimulator detects fibrillation (also referred to as ventricular fibrillation), i.e., irregular high-frequency intrinsic activity of the heart, which results in incomplete contraction of the affected cardiac chamber. Such fibrillation is included in tachycardia arrhythmia, which in addition to fibrillation also includes tachycardia (for example, ventricular flutter). In contrast to fibrillation, tachycardia routinely results in complete contraction of the affected cardiac chamber, but at a rate that is higher than physiologically appropriate. Such tachycardia may often be treated by antitachycardia stimulation, without the need for a defibrillation shock. Fibrillation is generally treated by defibrillation shock.

For detection of ventricular fibrillation, a detector is typically provided as a component of a control unit for the cardiac stimulator, and is connected to the right ventricular sensing unit and is designed to detect primary ventricular fibrillation on the basis of a right ventricular, bipolarly derived intracardiac electrocardiogram (IEGM). If a specified detection condition is met (e.g., when X of Y criteria are met), the detector indicates ventricular fibrillation.

For tachycardia of the ventricle, a distinction is made between conducted supraventricular tachycardia (SVT), which originates in the atrium, and ventricular tachycardia (VT), which originates in the ventricle itself. The type of ventricular tachycardia (ventricular tachycardia (VT) or supraventricular tachycardia (SVT)) is important for the treatment initiated after tachycardia is detected.

Tachycardia and fibrillation may be treated in various known ways by use of intracardiac electrotherapy. Antitachycardia stimulation (antitachycardia pacing, ATP) is often provided in the form of overdrive stimulation, in which stimulation pulses are delivered at a stimulation rate that is increased compared to the existing intrinsic (tachycardial) heart rate. Overdrive stimulation is intended to interrupt a reentry cycle of excitation of the myocardium, which is typical for ventricular tachycardia (VT, ventricular flutter), by means of a stimulation pulse provided before the natural (intrinsic) excitation of the affected cardiac chamber. For this purpose it is necessary to reliably detect intrinsic ventricle contractions before the pulse is initiated. Antitachycardia stimulation can also be provided via the delivery of a cardioversion shock or defibrillation shock, wherein the former usually has lower energy than the latter. Defibrillation shock is intended to make the entire myocardium of an affected cardiac chamber refractory at the same time, and thus to make the myocardium temporarily insensitive to excitation in order to thus interrupt circulating excitation of the affected cardiac muscle.

Previous methods for discriminating between ventricular tachycardia (VT) and supraventricular tachycardia (SVT) in single-chamber ICDs often result in inadequate therapies, because the intracardiac electrocardiograms (IEGMs) are evaluated only with respect to the intervals or changes thereto. Maximum sensitivity is always a priority—it is preferable to always detect actual VTs—and the specificity (detection of SVTs) is often unsatisfactory in prior methods. SVTs which are incorrectly classified as VTs result in a considerable number of inadequate defibrillator shocks, which are a physical and emotional burden on the affected patients. In addition, when ATP treatments are inadequate there is a risk of triggering dangerous ventricular tachycardia.

By use of morphological methods, the specificity of the SVT/VT discrimination may be improved without significantly limiting the sensitivity.

SUMMARY OF THE INVENTION

The invention seeks to improve detection performance (SVTNT discrimination) and thereby better differentiate ventricular tachycardia (VT), for which treatment using a cardioverter/defibrillator is necessary, from supraventricular tachycardia (SVT), for example conducted atrial flutter/defibrillation or conducted sinus tachycardia, for which ICD treatment is not necessary. The improved differentiation is preferably implemented within a device suitable for use within an ICD, and thus the device preferably has computational resources and power consumption appropriate for an ICD. The device preferably includes an automatic classification system which is capable of learning, operates on an individual patient basis, and contains the minimum possible number of parameters which must be adjusted by the medical practitioner. The classification is preferably be suitable for single- and/or multichamber cardioverters/defibrillators.

A preferred version of the invention involves a signal processing device for classifying intracardiac signals, having a signal input for a physiological signal (in particular an electrocardiogram); a morphology detection unit which is at least indirectly connected to the signal input; and a morphology discrimination unit. The morphology detection unit is designed:
  to detect signal maxima and minima in a portion of the signal (i.e., peak amplitudes within the signal portion), and for a specified number of signal maxima and minima, to determine in each case a peak value which is proportional to the magnitude of the peak amplitude, and
  from two adjacent peak values having opposite polarities, to determine a first type of peak-to-peak value as the sum of the absolute values of the individual peak values, and in the same signal portion, to determine additional peak-to-peak values of the first type (i.e., the sums of the absolute values of adjacent peak values having opposite polarities), and
  to normalize the peak-to-peak values to the largest of the determined peak-to-peak values, thus forming a specified number of normalized peak-to-peak values which together result in a morphology vector which is characteristic of the morphology of a particular signal portion.

The signal maximum or minimum can be regarded as the signal value between two zero crossings of the signal which has the greatest absolute value. A signal minimum has a negative algebraic sign, and a signal maximum has a positive algebraic sign. The peak-to-peak value results from addition of the absolute value of the amplitude value of the signal maximum and the absolute value of the amplitude value of the signal minimum. The signal maximum and the signal minimum are typically present in two directly adjacent subsections of the signal portion which are separated from one another by a zero crossing of the signal.

The detection unit preferably also determines peak-to-peak values of a second type as part of the morphology vector, with this second type being determined as the difference of the absolute values of adjacent peak values having the same polarity. These values of the second type are particularly calculated when a subsection of the signal portion is found which contains adjacent local signal maxima and/or adjacent local signal minima.

The morphology discrimination unit is connected to the morphology detection unit, and is designed to compare a particular morphology vector to at least one stored reference vector. This is preferably done by determining a distance between the particular morphology vector and the reference vector. A particular morphology vector can then be classified as supraventricular tachycardia or ventricular tachycardia depending on the distance from the reference vector.

Alternatively or preferably additionally, the morphology detection unit can:
  detect the amplitudes of the absolute signal maximum and the absolute signal minimum within a signal portion, and determine from their difference a third type of peak-to-peak value, and
  determine an area value which is proportional to an absolute area size included by the signal portion and the associated zero line, and to normalize this area value to the third type of peak-to-peak value, thus forming a normalized area value.

The morphology detection unit thus determines the signal maxima or minima present in the signal portion between two respective zero crossings of the signal, a signal minimum being understood to mean the respective largest peak amplitude having a negative algebraic sign.

The absolute area size refers to the area size which results between the zero line and a signal having the same direction within the signal portion, i.e., an area size without regard to the negative algebraic sign.

In this case the morphology discrimination unit is preferably designed to compare a particular normalized area value to at least one stored reference area value, and, depending on the magnitude of the difference between the particular normalized area value and the stored reference area value, to classify the particular normalized area value as supraventricular tachycardia or ventricular tachycardia.

In addition to the potentially high detection rate, the signal processing device offers the advantage that the foregoing methods for VT/SVT discrimination may be meaningfully supplemented and preferably combined with prior methods, for example, methods based on interval evaluation. Better classification results are expected from the combined use of morphology evaluation and rhythmological processes. Reducing incorrect detections improves the function of the instrument and thus enhances the patient's quality of life.

The signal processing device is preferably designed to automatically store a morphology vector as a reference vector, or alternatively or additionally, to automatically store an area value as an area reference value, when the signal processing device has detected that at least one condition is met which signifies that that the signal portion associated with the morphology vector is a segment of an electrocardiogram when a normal sinusoidal rhythm is present. In this case the signal processing device detects the presence of a stable sinusoidal rhythm over a time period, for example on the basis of rhythmological parameters such as heart rate and/or heart rate stability, and stores at least one morphology vector and/or area value generated in this time period as a reference vector or reference area value associated with a sinusoidal rhythm. The stored vector or value may subsequently be used for comparison with the respective current morphology vectors and/or area values. In this manner the signal processing device is always able to use current reference vectors or reference area values which are individualized to the patient.

With regard to evaluation of the respective current morphology vectors, the morphology discrimination unit is preferably designed to determine the Euclidean distance between the current morphology vector and the reference vector.

With regard to evaluation of the respective current area values, the morphology discrimination unit is preferably designed to determine the difference between the particular normalized area value and the stored reference area value, based on the absolute difference between the current area value and the reference value, divided by the reference value.

The signal processing device is preferably also designed to use a particular area value as well as a particular morphology vector for SVT/VT discrimination by determining a morphological distance based on the distance between the particular morphology vector and the reference vector, and the morphological difference between the particular normalized area value and the stored reference area value, and to compare these morphological distances to a decision threshold. A signal portion may then be classified as indicating ventricular tachycardia when the morphological distance from a reference vector associated with a sinusoidal rhythm, and/or from a reference area associated with a sinusoidal rhythm, is greater than the value of the decision threshold.

It is particularly preferred that the signal processing device be configured to automatically update the decision threshold during operation.

The SVT/VT discrimination may be further improved when the signal processing device is designed to evaluate not only signal morphology, but also a rhythmological parameter which is characteristic of a particular cardiac rhythm.

The signal processing device is preferably a component of an implantable cardioverter/defibrillator (ICD), in particular a single-chamber cardioverter/defibrillator. Since the signal processing device is able to perform VT/SVT discrimination solely on the basis of signal values detected from a ventricle, it is highly suitable for use in a single-chamber cardioverter/defibrillator.

Additional reference vectors and/or area reference values may be provided which are characteristic of conditions other than a sinusoidal rhythm, rather than using only reference vectors and/or area reference values indicative of a "normal" cardiac state. The additional vectors and/or areas may, for example, contain values which are typical for ventricular tachycardia. In this case the signal processing device is preferably designed to carry out a first comparison to the reference values that are characteristic of a sinusoidal rhythm, and to carry out a second comparison to the reference values that are characteristic of ventricular tachycardia, and to make a classification (VT/SVT discrimination) based on the results of both comparisons.

BRIEF DESCRIPTION OF THE DRAWINGS

Exemplary versions of the invention are explained in greater detail below with reference to the figures, which show the following.

DETAILED DESCRIPTION OF PREFERRED VERSIONS OF THE INVENTION

Figure 1:
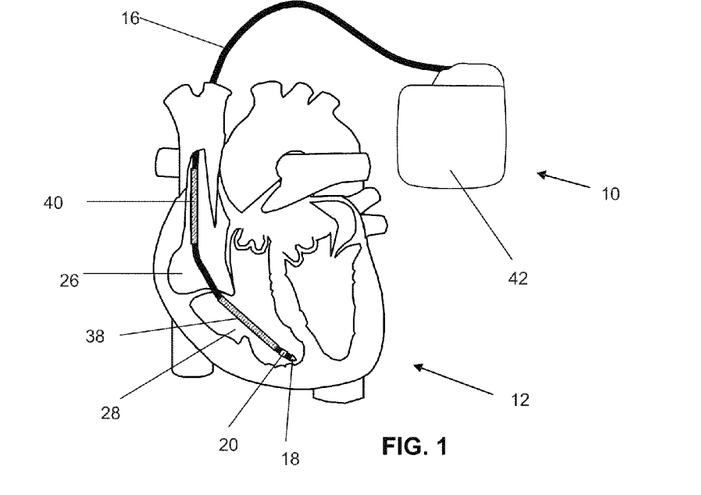
FIG. 1: shows a single-chamber cardioverter/defibrillator having a connected electrode line.

FIG. 1 shows an implant 10 in the form of a single-chamber cardiac pacemaker and cardioverter/defibrillator (ICD). A single electrode line, namely, a right ventricular electrode line 16, is attached to the cardiac stimulator 10. In the implanted state the right ventricular electrode line 16 terminates in the right ventricle 28 of the heart 12.

Figure 2:
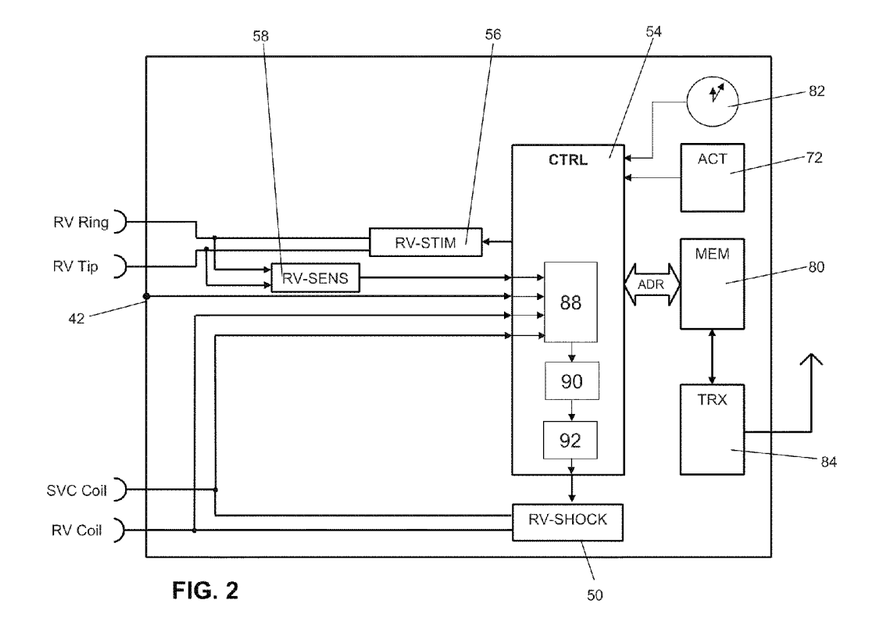
FIG. 2: schematically depicts several components of the single-chamber cardioverter/defibrillator of FIG. 1.

At its distal end the right ventricular electrode line 16 bears a right ventricular tip electrode 18 (also denoted RV Tip in FIG. 2), and at a slight distance therefrom, a right ventricular annular electrode 20 (also denoted RV Ring in FIG. 2). These electrodes are used to record electrical potentials in the right ventricle and to deliver stimulation pulses to the right ventricle during normal operation of the pacemaker.

The right ventricular electrode line 16 also bears a distal shock electrode 38 (also denoted RV Coil in FIG. 2) and a proximal shock electrode 40 (also denoted SVC Coil in FIG. 2) which are used to deliver defibrillation shocks in the event of ventricular fibrillation, i.e., in the event of (actual) ventricular fibrillation. The distal shock electrode 38 is situated in the right ventricle, and the proximal shock electrode 40 is situated in the superior vena cava (SVC).

FIG. 2 shows the main components of the cardiac stimulator 10 from FIG. 1. The electrical leads for the various electrodes RV Tip 18, RV Ring 20, RV Coil 38, and SVC Coil 40 are illustrated on the left side. Shock electrodes RV Coil 38 and SVC Coil 40 are connected to a right ventricular shock pulse generator 50. The shock generator 50 is connected to a stimulation control unit 54 which actuates the shock pulse generator 50 as needed to generate and deliver a defibrillation shock. In a preferred arrangement not illustrated in FIG. 2, the shock generator 50 also includes switching means via which either one or both of the shock electrodes 38 and 40 and/or the housing 42 are connected to the shock generator so that the defibrillation shock may be delivered via any given combination of shock electrodes 38 and 40 and housing 42.

The lead for the right ventricular tip electrode RV Tip 18 and the lead for the right ventricular annular electrode RV Ring 20 are each connected to a right ventricular stimulation unit 56 and to a right ventricular sensing unit 58. The right ventricular stimulation unit 56 and the right ventricular sensing unit 58 are each connected to the stimulation control unit 54.

The right ventricular stimulation unit 56 is designed to generate a right ventricular stimulation pulse on the basis of a control signal from the stimulation control unit 54, and to send the pulse to the right ventricular tip electrode RV Tip 18 in the lead for the right ventricular annular electrode RV Ring 20. Alternatively, the housing 42 of the cardiac stimulator 10 may form a neutral electrode, and the right ventricular stimulation unit 56 may be connected to the lead for the right ventricular annular electrode RV Tip 18 and to the housing 42 as the other electrode for delivery of a stimulation pulse. A right ventricular stimulation pulse differs from a defibrillation shock in that the stimulation pulse has a much lower pulse strength. Thus, unlike a defibrillation shock, it does not excite the entire cardiac tissue (myocardium) of a cardiac chamber upon a beat, but instead excites only the cardiac muscle cells in the immediate vicinity of the right ventricular tip electrode RV Tip 18. This excitation then propagates further over the entire right ventricle 28 via natural conduction, thus causing a stimulated contraction of the right ventricle 28.

The right ventricular sensing unit 58 is designed to initially amplify by means of an input amplifier and filter the electrical potentials present at the lead for the right ventricular annular electrode RV Ring 10 and the right ventricular tip electrode RV Tip 18. The right ventricular sensing unit 58 is also designed to evaluate the variation over time of the electrical signals present at the inputs thereof in such a way that the right ventricular sensing unit 58 automatically detects a natural (intrinsic), i.e., autonomous, contraction of the right ventricle 28. This may be achieved, for example, by comparing the variation over time of the signal present at the inputs of the right ventricular sensing unit 58 to a threshold value. The largest amplitude of the signal in the form of the so-called R wave is typically characteristic of a natural contraction of the right ventricle 28, which may be detected by comparing with the threshold value. This causes the right ventricular sensing unit 58 to emit a corresponding output signal to the stimulation control unit 54 which indicates a natural contraction of the right ventricle 28.

In a similar manner, one or more sensing units (not illustrated in FIG. 2) may also be provided for the shock electrodes RV Coil 38 and SVC Coil 40. These sensing units are preferably designed to detect signals between the shock electrodes 38 and 40, between the shock electrode 38 and housing 42, or between the shock electrode 40 and the housing 42. This is schematically illustrated in FIG. 2 by the connection of the shock electrodes 38 and 40 and the housing 42 to the electrocardiogram (EKG) detector 88.

Figure 3:
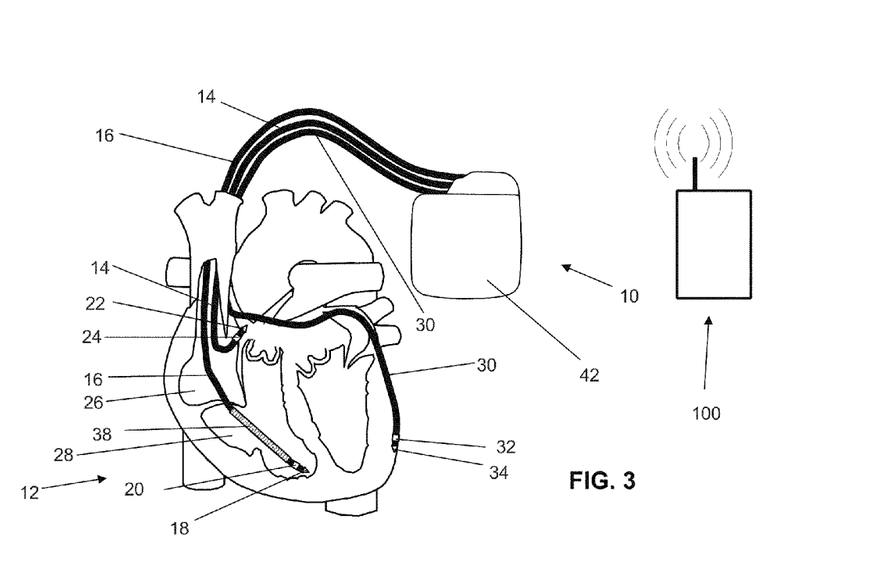
FIG. 3: shows a triple-chamber cardioverter/defibrillator having connected electrode lines.

FIG. 3 shows an implant 10 in the form of a biventricular triple-chamber cardiac pacemaker and cardioverter/defibrillator (ICD). Three electrode lines are connected thereto, namely, a right atrial electrode line 14, a right ventricular electrode line 16, and a left ventricular electrode line 30. In the implanted state the right atrial electrode line 14 terminates in the right atrium 26 of a heart 12, the right ventricular electrode line 16 terminates in the right ventricle 28 of the heart 12, and the left ventricular electrode line 30 extends over the coronary sinus of the heart 12 to the left ventricle of the heart.

At its distal end the right atrial electrode line 14 bears a right atrial tip electrode (RA Tip) 22, and at a slight distance therefrom, a right atrial annular electrode (RA Ring) 24. Similarly, at its distal end the right ventricular electrode line 16 bears a right ventricular tip electrode (RV Tip) 18, and at a slight distance therefrom, a right ventricular annular electrode (RV Ring) 20. Also attached at the distal end of the left ventricular electrode line 30 is a left ventricular tip electrode (LV Tip) 34, and at a slight distance therefrom, a left ventricular annular electrode (LV Ring) 32. These electrodes are used to record electrical potentials in the particular cardiac chamber, and to deliver stimulation pulses to the particular cardiac chamber during normal operation of the pacemaker.

In the implanted state, the right ventricular electrode line 16 also bears a right ventricular shock coil (RV Coil) 38 in the right ventricle as a defibrillation electrode.

Figure 4:
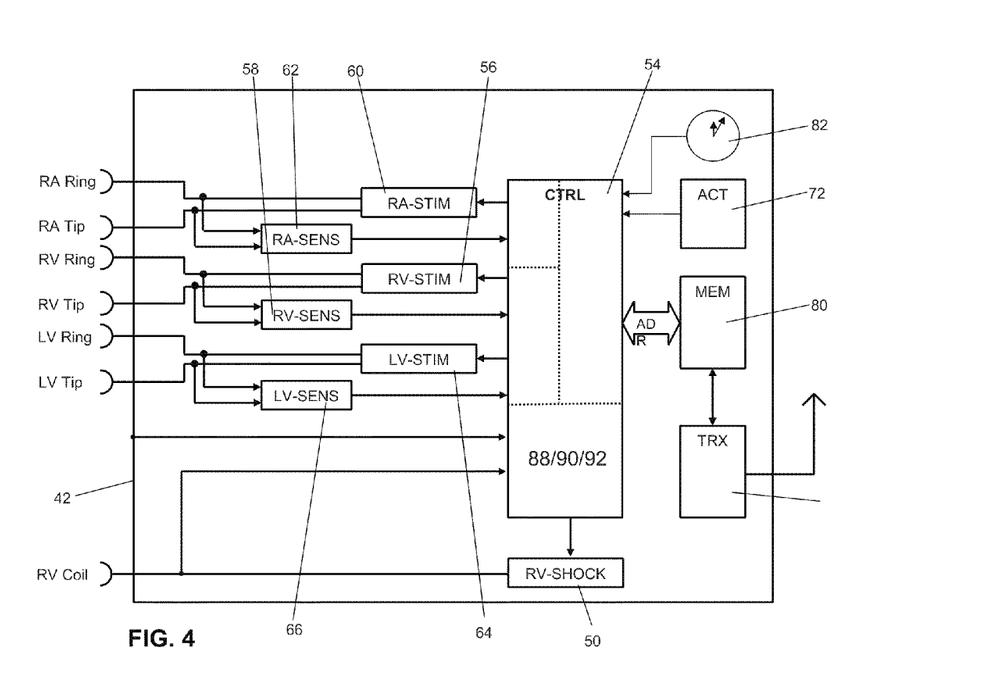
FIG. 4: schematically depicts several components of the single-chamber cardioverter/defibrillator of FIG. 3.

FIG. 4 illustrates the main components of the cardiac stimulator 10. Similarly as in FIG. 2, the electrical leads for the various electrodes RV Tip 18, RV Ring 20, RA Tip 22, RA Ring 24, LV Ring 32, LV Tip 34, and RV Coil 38 are illustrated on the left side. The (single) shock electrode RV Coil 38 is connected to a right ventricular shock pulse generator 50.

The statements provided above for FIG. 2 correspondingly apply to the right ventricular tip electrode RV Tip 18 and the right ventricular annular electrode RV Ring 20, housing 42 (as neutral electrode), the right ventricular stimulation unit 56, the right ventricular sensing unit 58, and the stimulation control unit 54.

Analogously, the lead for the right atrial tip electrode RA Tip 22 and the lead for the right atrial annular electrode RA Ring 24 are connected to a right atrial stimulation unit 60 and to a right atrial sensing unit 62, each of which in turn is connected to the stimulation control unit 54. The right atrial stimulation unit 60 is designed to generate stimulation pulses of sufficient strength to excite the right atrial myocardium. The right atrial stimulation pulses may have a different pulse strength than the right ventricular stimulation pulses. The right atrial sensing unit 62 is designed to detect, based on the variation over time of the difference signal present at the inputs thereof, a so-called P wave which characterizes a natural (intrinsic) contraction of the right atrium 26. If the right atrial sensing unit 62 detects a P wave, it generates an output signal and communicates it to the stimulation control unit 54, thereby indicating a natural contraction of the right atrium 26.

Similarly, the lead for the left ventricular tip electrode LV Tip 34 and the lead for the left ventricular annular electrode LV Ring 32 are also connected to a left ventricular stimulation unit 64 and a left ventricular sensing unit 66. The left ventricular stimulation unit 64 and the left ventricular sensing unit 66 are likewise connected to the stimulation control unit 54. Both function similarly to the previously described stimulation units 56 and 60 and sensing units 58 and 62.

Similarly, a sensing unit (not illustrated in FIG. 4) may also be provided for the shock electrode RV Coil 38. This sensing unit is preferably designed to detect signals between the shock electrode RV Coil 38 and the housing 42. This is schematically illustrated in FIG. 4 by the connection of the shock electrode 38 and the housing 42 to the EKG detector 88.

An acceleration sensor 72 is preferably integrated into the housing 42 of the cardiac stimulator 10, and connected to the stimulation control unit 54. The acceleration sensor 72 is designed to detect a motion signal as a function of the bodily activity of a patient, and to send a corresponding accelerometer output signal which indicates the bodily activity of the patient to the stimulation control unit 54. This allows the stimulation control unit 54 to adapt the timing of the stimulation pulses to the needs (hemodynamic demand) of the patient.

The cardiac stimulator 10 also includes a memory unit 80 which is connected to the stimulation control unit 54 and which allows storage of signals which are generated or evaluated by the stimulation control unit 54. Additionally or alternatively, the memory unit 80 preferably allows control programs for the stimulation control unit 54 to be stored in modifiable form. The stimulation control unit 54 is also connected to a timer 82.

The memory unit 80 is connected to a telemetry unit 84 which allows data stored in the memory unit 80 to be wirelessly transmitted to the external device 100, or allows program commands to be transmitted from the external device 100 to the cardiac stimulator 10 for storage in the memory unit 80.

For recording intracardiac electrocardiograms, the control unit 54 has an EKG detector 88 which is connected to the housing 42 of the cardiac stimulator 10 as a first electrode and which is also connected to the ventricular shock electrode RV Coil 38 as a second electrode. The electrocardiogram detector 88 is also connected to the sensing unit 58. The sensing unit 58 generates a ventricular marker signal whenever it detects a ventricular event. The electrocardiogram detector 88 uses this marker signal to detect a signal portion in its particular recorded electrocardiogram which contains a QRS complex. The particular signal portion of the intracardiac electrocardiogram detected by the electrocardiogram detector 88 is a signal portion in a time window around a QRS complex detected by the ventricular sensing unit 58. The duration of this time window may optionally be a function of the particular detected heart rate.

For a single-chamber cardioverter/defibrillator as illustrated in FIGS. 1 and 2, the control unit 54 is designed to reliably differentiate between supraventricular tachycardia (SVT) and ventricular tachycardia (VT), and when the latter is ventricular fibrillation (VF), the control unit 54 is designed to trigger delivery of a ventricular defibrillation shock via the shock pulse generator 50 and the shock electrodes RV Coil 38 and/or 40 connected thereto.

For this purpose, the control unit has a morphology detection unit 90 which has a first signal analysis unit including a peak value detector designed to detect global maxima and minima of the signal in a signal portion of the intracardiac EKG having a QRS complex, and to determine an absolute largest signal amplitude, as well as the largest signal amplitude of opposite polarity which is adjacent to the absolute largest signal amplitude. The morphology detection unit uses the difference between these two peak amplitudes to generate a first type of peak-to-peak value for the signal portion being analyzed. The morphology detection unit also determines a second type of peak-to-peak value as the difference in the absolute values of adjacent peak values of the same polarity, and determines a third type of peak-to-peak value as the difference in the amplitudes of the absolute signal maximum and the absolute signal minimum. A second signal analysis unit of the morphology detection unit is designed to determine an area value which corresponds to the area size of an area included by the EKG signal portion and the associated zero line.

The morphology detection unit is also designed to normalize at least some peak-to-peak values of the signal portion to the largest peak-to-peak value of the signal portion. Similarly, the morphology detection unit is also designed to normalize the area value formed by the second signal analysis unit to the third type of peak-to-peak value which belongs to the same signal portion of the EKG signal. Based on the normalized amplitude values for a particular signal portion, the morphology detection unit generates a morphology vector which characterizes the morphology of this signal portion, as described in greater detail below.

The morphology detection unit 90 sends this morphology vector and the area value which is normalized to the third type of peak-to-peak value to a morphology discrimination unit 92. The morphology discrimination unit is designed to compare a particular current morphology vector and a particular current normalized area value to reference values stored in the memory 80, and to determine the Euclidean distance from a vector containing the morphology vector and the normalized area value, to one or more corresponding stored reference vectors. This is also described in greater detail below. One of the stored reference vectors is preferably associated with the normal sinusoidal rhythm, whereas a further stored reference vector may be associated with ventricular tachycardia (VT), for example.

When the calculation of the Euclidean distance from one or more reference vectors indicates that the current vector is closer to the reference vector associated with the normal sinusoidal rhythm, a current tachycardia is classified as supraventricular tachycardia. Otherwise, the current tachycardia is classified as ventricular tachycardia. If the comparison of the Euclidean distance with multiple reference vectors indicates that the distance from a current vector to a reference vector characterizing ventricular tachycardia is less than the distance to the reference vector characterizing the normal sinusoidal rhythm, a particular current signal portion is associated with ventricular tachycardia. In the event of association with ventricular tachycardia, optionally taking other conditions into account, the control unit 54 may initiate delivery of a defibrillation shock via the shock pulse generator 50 and the shock electrodes connected thereto.

In this manner the morphology discrimination unit assesses the signal form of the QRS complexes. During a sinusoidal rhythm, the morphology remains essentially stable. For supraventricular tachycardia each cardiac excitation, as for the sinusoidal rhythm, originates in the atrium (even if not necessarily in the sinus node) or in the AV node, so that the conduction and propagation in the ventricle is usually very similar to that in the sinusoidal rhythm. However, if ventricular tachycardia is present the excitation propagation in the ventricle is normally very different from that in the sinusoidal rhythm, which results in a different signal morphology (see FIG. 5). Thus, VTs may be differentiated from SVTs by evaluating the morphology.

Figure 5:
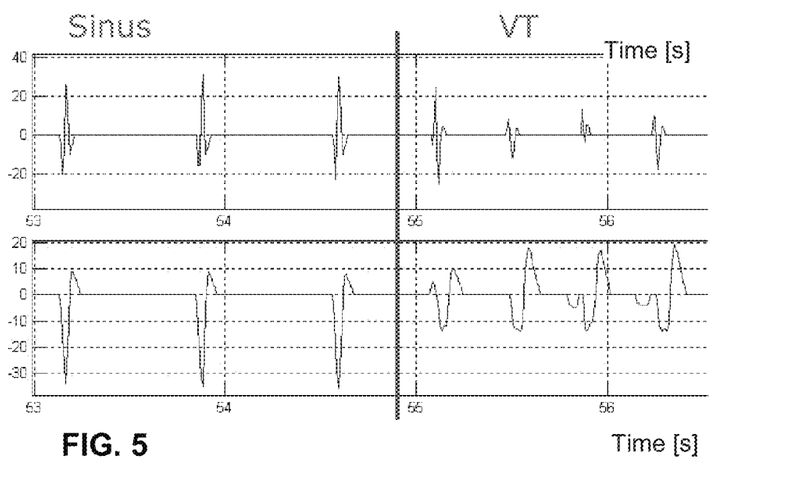
FIG. 5: shows examples of intracardiac electrocardiograms for the case of excitation of the ventricle via the AV node, which also occurs in supraventricular tachycardia (denoted as "Sinus" in FIG. 5), and in ventricular tachycardia (denoted as "VT" in FIG. 5)

FIG. 5 shows examples of intracardiac electrocardiograms for the case of excitation of the ventricle via the AV node, which also occurs in supraventricular tachycardia (denoted as "Sinus" in FIG. 5), and in ventricular tachycardia (denoted as "VT" in FIG. 5). The upper intracardiac electrocardiograms are derived via the right ventricular annular electrode RV Ring 20 and the right ventricular tip electrode RV Tip 18, whereas the two lower intracardiac electrocardiograms in FIG. 5 are derived via the ventricular shock coils (RV Coil) 38 and (SVC Coil) 40.

The signal processing device formed by the morphology detection unit 90 and the morphology discrimination unit 92, which is implemented by the control unit 54 for the implant 10, preferably carries out two analytical methods, namely, a morphology analysis based on the signal peak amplitudes (signal waves)—also referred to below as the wave difference method—and an analysis based on a peak-to-peak value of the third type of normalized area which is included by the signal and the particular zero line in the signal portion.

Figure 6:
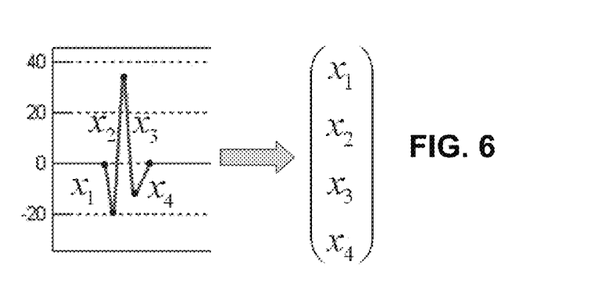
FIG. 6: shows a morphology analysis based on the wave difference method.

In the wave difference method (see FIG. 6), the signal peaks (peak amplitudes) between zero crossings are searched, and a vector is generated from the differences in the amplitude values of adjacent peak amplitudes. In the example, the vector components are formed from the difference between zero and the first peak amplitude, the first peak amplitude and the second peak amplitude, the second peak amplitude and the third peak amplitude, and the third peak amplitude and zero. All amplitude difference values are normalized to the maximum amplitude difference, i.e., the largest of all of the peak-to-peak values. The maximum amplitude difference is stored separately. The peak-to-peak values $X_2$ and $X_3$ illustrated in FIG. 6 are peak-to-peak values of the first type. In addition, the peak-to-peak value $X_2$ is the peak-to-peak value of the third type, namely, the absolute largest difference between peak values in the illustrated signal portion. Throughout this document, the peak-to-peak values are also referred to as wave differences. It is these values that are combined into a vector.

A reference vector is generated in the sinusoidal rhythm. For an onset of tachycardia the vectors of the QRS complexes may then be compared to the reference vector. The Euclidean distance or another measure of distance may be used for this purpose.

One advantage of the wave difference method is that small amplitude fluctuations or zero line fluctuations have only minor effects on the morphology calculation.

In the normalized area method (see FIG. 7) a morphological value—a normalized area—is calculated by dividing the total area of the QRS complex by the maximum amplitude difference between peak values, i.e., the value of the third type.

Figure 7:
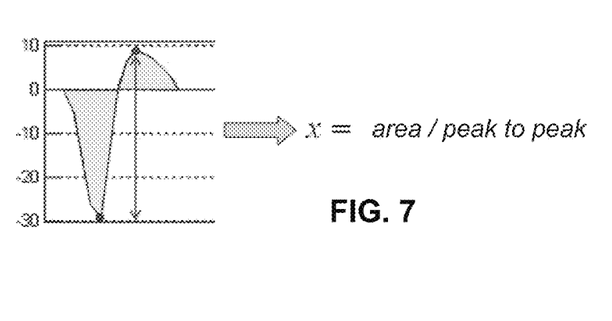
FIG. 7: shows a morphology analysis based on the method of normalized total area of the QRS complex.

One advantage of the normalized area method is that scattering of individual sample values is practically insignificant, since all sample values of a QRS complex are included in the calculation. Zero line fluctuations have very little effect on the area and the peak-to-peak value.

The normalized area method is preferably combined with the wave difference method to achieve a better classification result than if only a single method was used. An independent reference is formed for each method. The particular normalized measures of distance for the reference values (reference vector and reference area value) determined by the two methods are averaged to obtain a combined "morphological distance."

A classification may then be made based on a decision threshold. If the morphological distance is below the threshold, this indicates similarity to the reference. Values above the threshold indicate a different signal origin. This is illustrated in detail in FIG. 11 with reference to a flow diagram.

When determining the reference values which characterize a sinusoidal rhythm, the morphological values—i.e., the morphology vector and normalized area size—in the sinusoidal rhythm are calculated for each QRS complex (i.e., for each ventricular sense event). In each case, a signal portion containing a QRS complex is excerpted from the intracardiac electrocardiogram (IEGM) derived, for example, via the shock coil (RV Coil) 38 and the housing 42, and the morphological features are extracted. The amplitude differences of the waves are calculated, normalized to the absolute maximum difference, and written into a vector. The vector length is set at 4, for example. The absolute area of the QRS complex is also calculated and normalized to the maximum peak-to-peak amplitude (i.e., the peak-to-peak value of the third type). These two reference values are stored. Various methods may be used for the reference calculation, for example, they can be derived continuously or at intervals (for example, every 12 hours). The sinusoidal rhythm may be determined using a frequency relation, for example.

When tachycardia occurs, the wave differences and the normalized area of each QRS complex are compared to their respective reference, and the "morphological distance" is calculated therefrom. The classification is made on the basis of an individual patient dynamic decision threshold: if the distance is below the critical threshold, this indicates greater similarity to the reference and a determination of SVT. If the distance is above the critical threshold, there is lesser similarity and a determination of VT. The resulting decision generated by the morphology algorithm may then be combined with other criteria for the ICD, so that the treatment is either suppressed (for SVT) or enabled (for VT).

In the wave difference method, the comparison to the relevant reference vector can be done by calculating the Euclidean vector distance:

$$\begin{pmatrix} x_{ref1} \\ x_{ref2} \\ x_{ref3} \\ x_{ref4} \end{pmatrix} - \begin{pmatrix} x_1 \\ x_2 \\ x_3 \\ x_4 \end{pmatrix} = \vec{e} \longrightarrow \begin{array}{c} \text{Euclidean distance} \\ d = \sqrt{\vec{e}^T \cdot \vec{e}} \end{array}$$

Figure 9:
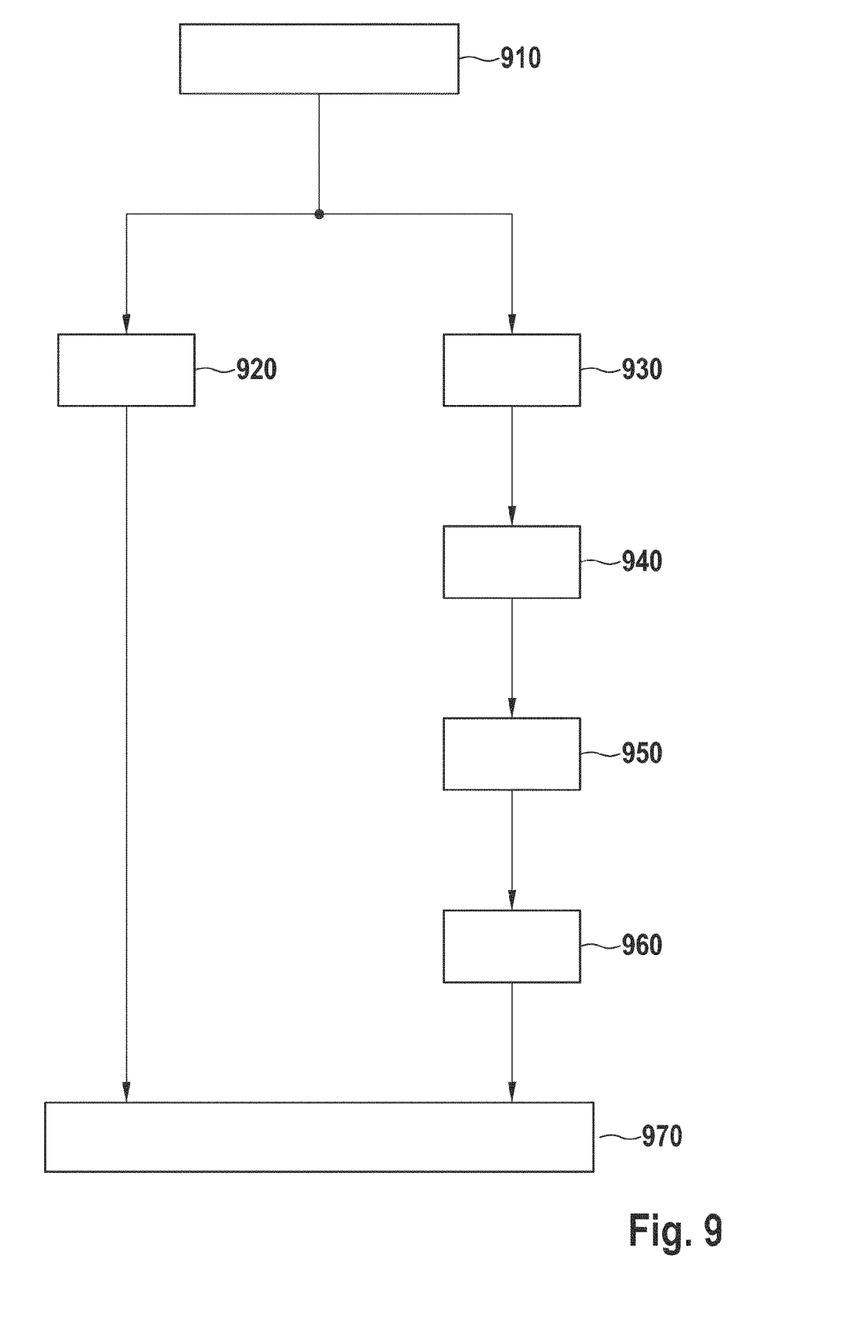
FIG. 9: shows a flow diagram illustrating the determination of a particular morphology vector.

FIG. 9 shows a flow diagram illustrating preferred steps for determining a morphology vector. In a first step 910, the morphology detection unit determines the current QRS complex. For example, the current QRS complex corresponds to a signal variation over a time span of 250 ms. Once this is done, steps 920 and 930-960 can occur in parallel. In step 920, the morphology detection unit determines the normalized area as the quotient of the QRS complex area value and the peak-to-peak value of the third type (i.e., the maximum difference between peak values). Along the parallel path, in step 930, the morphology detection unit determines zero crossings in the QRS complex, waves, and peak-to-peak values (wave differences), as described above in reference to FIG. 6. In the subsequent step 940, the morphology detection unit eliminates all wave differences whose absolute value is less than or equal to 5% of the absolute value of the maximum wave difference. In step 950, the morphology detection unit normalizes the values of the remaining wave differences to the absolute value of the maximum wave difference (i.e., to the value of the third type), and generates a multidimensional (e.g., four-dimensional) vector, wherein the normalized wave differences form scalars of this vector. In step 960, the morphology detection unit also stores the value of the maximum wave difference. In step 970, the morphology detection unit transmits the normalized area value and the multidimensional vector to the morphology discrimination unit.

Figure 8:
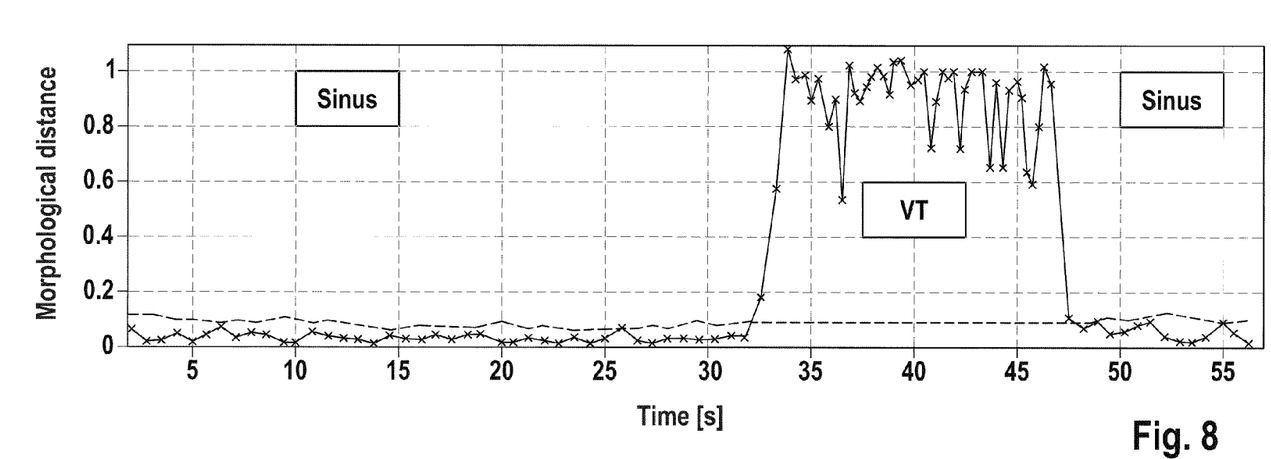
FIG. 8: shows an example of a sequence of a classification by comparing the morphological distance to a decision threshold.

In the normalized area method, the difference between a normalized area and a reference area value is used to indicate VT or SVT. Where the normalized area method and the wave difference method are both used together, the results of the two methods (i.e., the difference between the normalized area and the reference area value, and the difference between the morphology vector and the reference vector) can be combined—for example, by averaging them—to obtain a morphological distance. The classification can then be made by comparing the morphological distance to a decision threshold, as illustrated in FIG. 8.

In the wave difference method, each morphology vector must be compared to the reference vector. However, it may occur that the vectors are shifted relative to one another. In this case it is first necessary to perform alignment. For this purpose the current morphology vector and the respective reference vector are shifted relative to one another, and the Euclidean distance is calculated for each shift. The relative deviation of the maximum amplitude difference for the current complex is added thereto for reference. The minimum distance (for the shifts) is regarded as the distance value for the current QRS complex.

Figure 10:
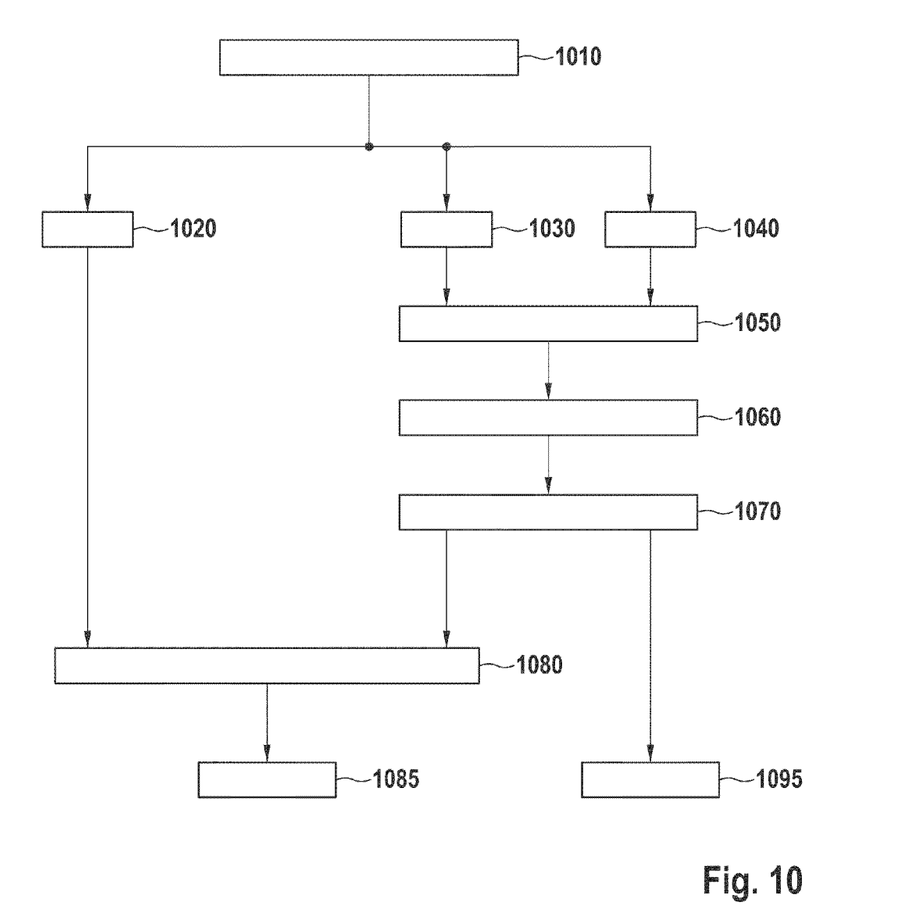
FIG. 10: shows a flow diagram illustrating a preferred determination of the morphological distance of a morphology vector of a QRS complex from a reference vector.

FIG. 10 shows a flow diagram illustrating preferred steps for determining the morphological distance of a morphology vector of a QRS complex to a reference vector. In a first step 1010, the morphology discrimination unit receives values from the morphology detection unit. In steps 1020, 1030, and 1040, the morphology discrimination unit makes an adjustment: in step 1020 a normalization is carried out by dividing an absolute difference of the current normalized area value and the normalized area reference value by the normalized area reference value. In step 1030, the morphology discrimination unit expands the current wave difference vector by one or more dimensions; for the case of a four-dimensional wave difference vector an expansion by three dimensions is carried out. The scalars of the added dimensions each have a value of zero. Likewise, in step 1040 the morphology discrimination unit expands the reference vector to the same number of dimensions as the expanded wave difference vector; i.e., for the case of a four-dimensional wave difference vector, an expansion is made to seven dimensions. Here as well, the scalars of the added dimensions have a value of zero.

In step 1050, the morphology discrimination unit calculates the Euclidean distance for four shifts of the current vector relative to the reference vector. In step 1060, the morphology discrimination unit takes into account the relative deviation of the value of the maximum wave difference (i.e., the peak-to-peak value of the third type) with respect to the reference value. In step 1070, the morphology discrimination unit determines the distance value for the reference vector as the minimum Euclidean distance.

In step 1080, the morphology discrimination unit averages this distance value with the value determined in step 1020, the normalized area distance. In step 1085, the morphology discrimination unit outputs this average value of the two normalized distances as the morphological distance. In step 1095, the morphology discrimination unit also stores an optimal shift of the current vector.

In the normalized area method, the morphological distance is formed from the absolute difference of the current area value and the reference value. This difference is normalized to the reference value. The "distance value" thus indicates the relative difference with respect to the reference value for the area value:

$$\text{Area distance} = |(\text{normArea}_{ref} - \text{normArea}_{current})|/\text{normArea}_{ref}$$

The average value of the distance of the normalized area and the distance of the wave differences is formed as the total distance result for a QRS complex.

For the Euclidean distance, for computational reasons the square root may be omitted. The result then corresponds to the quadratic distance.

For each patient, an individual dynamic decision threshold is calculated which is automatically adjusted to each heartbeat, and thus is automatically updated during operation of the signal processing device. This is meaningful due to the fact that the scattering of the intracardiac signals may be very different for various patients. QRS complexes whose measure of distance is above the morphology threshold are classified as VT beats, and those under the threshold are classified as SVT beats.

Figure 11:
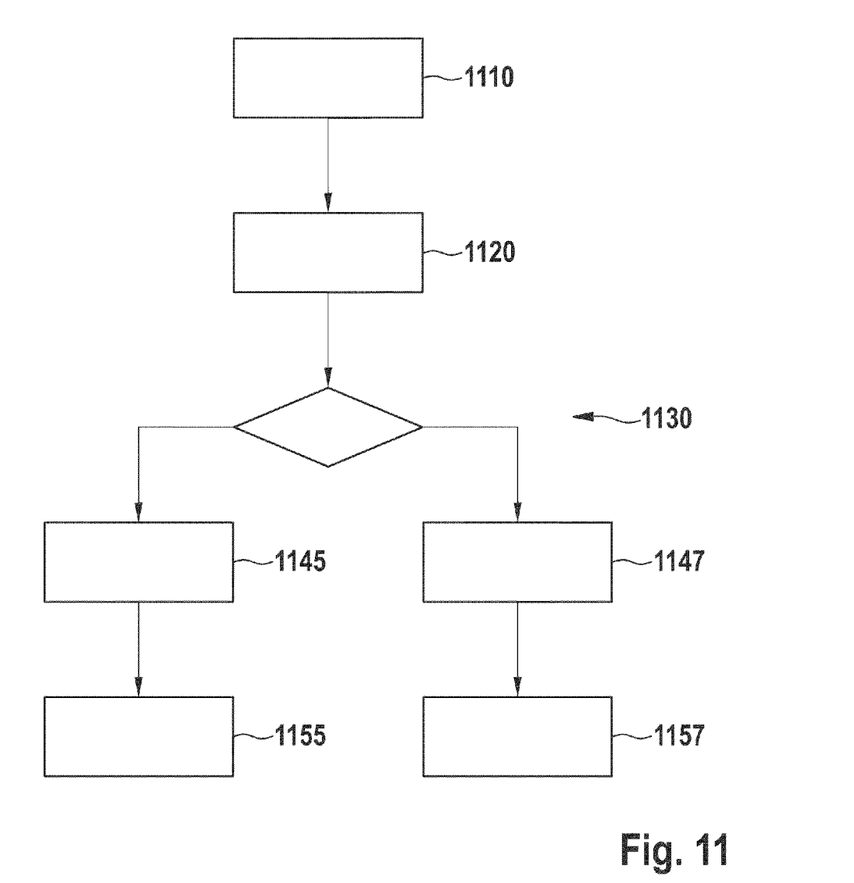
FIG. 11: shows a flow diagram illustrating the VT/SVT discrimination based on the morphological distance and a decision threshold.

FIG. 11 illustrates a preferred VT/SVT discrimination method based on the morphological distance and a decision threshold. The algorithm begins as soon as the heart rate has exceeded a given threshold value. At the beginning, two counter variables are set to zero. Steps 910 through 970 are essentially carried out in step 1110, i.e., the determination of the morphology vector previously explained with respect to FIG. 9. In addition, a first counter variable is increased by 1. Steps 1010 through 1085 are essentially carried out in step 1120, i.e., the determination of the morphological distance which was previously explained in the description for FIG. 10.

In step 1130, the morphology discrimination unit compares the value of the morphological distance to the value of the decision threshold. If the value of the morphological distance is greater than the value of the decision threshold, in step 1145 the morphology discrimination unit classifies the current QRS complex as ventricular tachycardia, and in step 1155 increases the value of a second counter variable by 1. Alternatively, in step 1147 the morphology discrimination unit classifies the current QRS complex as supraventricular tachycardia or sinusoidal rhythm, and reduces the value of the second counter variable by 1 (but only if the value of the second counter variable is greater than zero). As long as the heart rate has exceeded a given threshold value the algorithm is repeated, starting with step 1110.

The stimulation control unit is able to control the treatment based on the value of the two counter variables. Thus, for example, a decision may be made that ventricular tachycardia is present when the value of the second counter variable is greater than one-half the value of the first counter variable.

It will be apparent to those skilled in the art that numerous modifications and variations of the described examples and versions of the invention are possible in light of the above teaching. The disclosed examples and versions are presented for purposes of illustration only, and it is the intent to cover all modifications and alternate versions that are literally encompassed by the claims below, or which are equivalent to such modifications and alternate versions.

What is claimed is:

1. An intracardiac signal processing device including:
   a. a morphology detection unit configured to:
   (1) receive a signal representing an electrocardiogram or a portion thereof;
   (2) determine peak values representing magnitudes of the maxima and minima within the signal,
   (3) determine peak-to-peak values of a first type from adjacent peak values having opposite polarities, each peak-to-peak value of the first type representing a sum of the absolute values of the adjacent peak values therein,
   (4) define a morphology vector from the peak-to-peak values of the first type, the morphology vector characterizing the morphology of the signal;

b. a morphology discrimination unit in communication with the morphology detection unit, the morphology discrimination unit being configured to:
  (1) compare the morphology vector to a stored reference vector, and
  (2) classify the morphology vector as indicative of supraventricular tachycardia or ventricular tachycardia in dependence on the comparison.

2. The signal processing device of claim 1 wherein:
a. the morphology detection unit is configured to:
  (1) determine the largest of the peak-to-peak values of the first type, this largest value defining a peak-to-peak value of a third type,
  (2) normalize the peak-to-peak values of the first type with respect to the peak-to-peak value of the third type,
b. the morphology vector is defined from the normalized peak-to-peak values.

3. The signal processing device of claim 1 wherein the morphology vector is defined from at least four peak-to-peak values of the first type.

4. The signal processing device of claim 1 wherein the morphology discrimination unit is configured to:
a. compare the morphology vector to the stored reference vector by determining a distance between the morphology vector and the stored reference vector, and
b. classify the morphology vector as indicative of supraventricular tachycardia or ventricular tachycardia in dependence on the distance.

5. The signal processing device of claim 1 wherein:
a. the morphology detection unit is further configured to:
  (1) determine an area value representing an absolute area size defined by the signal;
  (2) normalize the area value with respect to the peak-to-peak value of the third type, thereby defining a normalized area value,
b. the morphology discrimination unit is further configured to:
  (1) compare the normalized area value to a stored reference area value, and
  (2) classify the normalized area value as indicative of supraventricular tachycardia or ventricular tachycardia in dependence on the magnitude of the difference between the normalized area value and the stored reference area value.

6. The signal processing device of claim 5 wherein the device:
a. further includes a stimulation electrode, and
b. is configured to deliver electrical stimulation via the stimulation electrode in dependence on both:
  (1) the classification of the morphology vector, and
  (2) the classification of the normalized area value.

7. The signal processing device of claim 1 wherein the device is configured to:
a. detect when a normal sinusoidal rhythm of a heart is present, and
b. store the morphology vector as a reference vector when the device has detected the presence of a normal sinusoidal heart rhythm.

8. The signal processing device of claim 1 wherein the morphology discrimination unit is configured to determine the Euclidean distance between the morphology vector and the stored reference vector.

9. The signal processing device of claim 1 wherein the device is also configured to:
a. determine one or more parameters characterizing the rhythm of the heart, and
b. compare the determined parameters to parameters indicating normal and/or abnormal heart rhythm.

10. The signal processing device of claim 1 wherein the morphology detection unit is further configured to determine peak-to-peak values of a second type, each peak-to-peak value of the second type representing the difference of the absolute values of adjacent peak values having the same polarity.

11. An intracardiac signal processing method including the steps of:
a. obtaining a signal representing an electrocardiogram or a portion thereof;
b. determining peak values within the signal, the peak values representing magnitudes of the maxima and minima within the signal,
c. determining peak-to-peak values of a first type from adjacent peak values having opposite polarities, each peak-to-peak value of the first type representing a sum of the absolute values of the adjacent peak values therein,
d. defining a morphology vector from the peak-to-peak values of the first type, the morphology vector characterizing the morphology of the signal;
e. comparing the morphology vector to a stored reference vector; and
f. delivering electrical stimulation to a heart at least partially in dependence on the comparison.

12. The intracardiac signal processing method of claim 11 further including the steps of:
a. determining a peak-to-peak value of a third type, the peak-to-peak value of the third type representing the largest of the peak-to-peak values of the first type, and
b. normalizing the peak-to-peak values of the first type with respect to the peak-to-peak value of the third type,
wherein the morphology vector is defined from the normalized peak-to-peak values.

13. The intracardiac signal processing method of claim 12 further including the steps of:
a. determining an area value representing an absolute area size defined by the signal, and
b. normalizing the area value with respect to the peak-to-peak value of the third type,
c. comparing the normalized area value to a stored reference area value, and
d. delivering electrical stimulation to a heart at least partially in dependence on both:
  (1) the comparison between the normalized area value and the stored reference area value, and
  (2) the comparison between the morphology vector and the stored reference vector.

14. The intracardiac signal processing method of claim 13 wherein electrical stimulation is delivered to the heart if:
a. the difference between the normalized area value and the stored reference area value, and
b. the difference between the morphology vector and the stored reference vector, both exceed a difference threshold.

15. An intracardiac signal processing device including:
a. a morphology detection unit configured to:
  (1) receive a signal representing an electrocardiogram or a portion thereof;
  (2) determine peak values representing magnitudes of the maxima and minima within the signal,
  (3) determine from adjacent peak values having opposite polarities peak-to-peak values of a first type, each peak-to-peak value of the first type representing sums of the absolute values of the two adjacent peak values therein, (4) determine a peak-to-peak value of a third type, the peak-to-peak value of the third type representing an absolute difference between the peak values of the greatest maximum and the smallest minimum within the signal, (5) normalize the peak-to-peak values of the first type with respect to the peak-to-peak value of the third type, the normalized peak-to-peak values defining a morphology vector characterizing the morphology of the signal, b. a morphology discrimination unit in communication with the morphology detection unit, the morphology discrimination unit being configured to:

(1) compare the morphology vector and a stored reference vector, and (2) trigger delivery of electrical stimulation to the heart at least partially on the basis of the comparison.

16. The signal processing device of claim 15 wherein:

a. the morphology detection unit is further configured to:

(1) determine an area value representing an absolute area size defined by the signal, and (2) normalize the area value with respect to the peak-to-peak value of the third type, b. the morphology discrimination unit is further configured to:

(1) compare the normalized area value to a stored reference area value, and (2) trigger delivery of electrical stimulation to the heart on the basis of both:

(a) the comparison of the morphology vector and the stored reference vector, and (b) the comparison of the normalized area value and the stored reference area value.

17. The signal processing device of claim 16 wherein the morphology detection unit is configured to:

a. compare the morphology vector and the stored reference vector by calculating the distance therebetween, and b. compare the normalized area value and the stored reference area value by calculating the difference therebetween.

18. The signal processing device of claim 15 wherein:

a. the morphology detection unit is further configured to:

(1) determine an area value representing an absolute area size defined by the signal, and (2) normalize the area value with respect to the peak-to-peak value of the third type, b. the morphology discrimination unit is further configured to:

(1) classify the normalized area value as indicative of supraventricular tachycardia or ventricular tachycardia in dependence on the degree of similarity between the normalized area value and a stored reference area value, and (2) classify the morphology vector as indicative of supraventricular tachycardia or ventricular tachycardia in dependence on the degree of similarity between the morphology vector and the stored reference vector.

19. An intracardiac signal processing device including:

a. a morphology detection unit configured to:

(1) receive a signal representing an electrocardiogram or a portion thereof;

(2) determine peak values representing the magnitudes of the maxima and minima within the signal, (3) determine a third type of peak-to-peak value, the third type representing the absolute difference between the peak values of the greatest maximum and the smallest minimum within the signal, (4) determine an area value representing an absolute area size defined by the signal, (5) normalize the area value with respect to the third type of peak-to-peak value, thereby defining a normalized area value, b. a morphology discrimination unit in communication with the morphology detection unit, the morphology discrimination unit being configured to:

(1) compare the normalized area value to at least one stored reference area value, and (2) classify the normalized area value as indicative of supraventricular tachycardia or ventricular tachycardia in dependence on the comparison.

20. The intracardiac signal processing device of claim 19 wherein:

a. the morphology detection unit is further configured to:

(1) determine from adjacent peak values having opposite polarities peak-to-peak values of a first type, each peak-to-peak value of the first type representing the sum of the absolute values of the adjacent peak values therein, (2) normalize the peak-to-peak values of the first type with respect to the peak-to-peak value of the third type, the normalized peak-to-peak values defining a morphology vector characterizing the morphology of the signal, b. the morphology discrimination unit is further configured to:

(1) compare the morphology vector to a stored reference vector, and (2) classify the morphology vector as indicative of supraventricular tachycardia or ventricular tachycardia in dependence on the comparison.

* * * * *